United States Patent
Yoon

Patent Number: 6,165,281
Date of Patent: Dec. 26, 2000

[54] METHOD FOR REMOVING GLASS PARTICLES ADHERED TO THE INNER WALL OF A GLASS CARTRIDGE OF AN INJECTION SYRINGE

[75] Inventor: Yeo Saeng Yoon, Seoul, Rep. of Korea

[73] Assignee: Boo Yoon Tech, Inc., Seoul, Rep. of Korea

[21] Appl. No.: 09/511,731

[22] Filed: Feb. 23, 2000

[30] Foreign Application Priority Data

Apr. 27, 1999 [KR] Rep. of Korea ........................ 99-15069

[51] Int. Cl.$^7$ ........................................................ B08B 9/087
[52] U.S. Cl. ................. 134/8; 134/6; 134/7; 134/22.1; 134/22.11; 134/22.12; 134/22.14; 134/22.18; 134/22.19; 134/42; 15/23; 15/207.2; 15/104.09; 15/104.095; 510/161; 451/51; 451/59; 451/61
[58] Field of Search ...................... 15/104.09, 104.095, 15/207.2, 23; 510/161; 451/61, 51, 59; 134/6, 7, 8, 22.1, 22.11, 22.12, 22.14, 22.18, 22.19, 42

[56] References Cited

U.S. PATENT DOCUMENTS

| | | | |
|---|---|---|---|
| 5,690,544 | 11/1997 | Sakurai | 451/444 |
| 5,755,894 | 5/1998 | Bowman et al. | 134/22.12 |
| 5,802,667 | 9/1998 | Williams | 15/395 |

OTHER PUBLICATIONS

Saunders, Organic Polymer Chemistry–An Introduction to the Organic Chemistry of Adhesives, Fibres, Paints, Plastics and Rubbers, Second Edition, p. 193, 1973.

*Primary Examiner*—Sharidan Carrillo
*Attorney, Agent, or Firm*—McGuireWoods, LLP

[57] ABSTRACT

A method of removing glass particles adhering to an inner wall of a glass cartridge of an injection syringe. A helical brush remover made of polyhexamethylene dodecanediamide or a helical stone remover made of aluminum oxide and titanium oxide is inserted into the inner wall of the glass cartridge. The helical brush or helical stone remover rubs against the inner wall of the glass cartridge to remove glass particles as water is sprayed onto the inner wall of the glass cartridge.

2 Claims, 2 Drawing Sheets

METHOD FOR REMOVING GLASS PARTICLES ADHERED TO THE INNER WALL OF A GLASS CARTRIDGE OF AN INJECTION SYRINGE

BACKGROUND OF THE INVENTION

1. Field of the Invention

The present invention relates to a method to remove glass particles deposited on the inner wall of a glass injection syringe and more particularly, to a method to completely remove glass particles produced during a manufacturing process and later adhered to the inner wall of a glass injection syringe thus being mistakenly injected into the bloodstream of a human body.

2. Description of the Prior Art

There are various types of injections (e.g., ampules, vials, bottles, etc.) classified according to the containers into which each injection is inserted. In general, injection containers are made of either glass or plastic and glass is often more preferred.

The way each injection is prepared varies depending on the container of each injection material. For example, ampule-type injection containers usually produce a lot of broken glass particles when severed by medical operators to prepare injections while vial-type containers often produce broken rubber fragments when a reciprocating movement is performed a few times to suck a given pharmaceutical liquid. The problems of inconveniences in medical practices and the environmental contamination resulted from using the above injection containers have been much resolved since the introduction of 'prefilled syringe'. The prefilled glass syringe, being prefilled with a certain pharmaceutical liquid, can easily deliver the injection through a patient's blood vessels or muscles without much difficulties; however, it also had the drawback of not being able to prevent minute glass particles adhered to the inner wall of a glass injection syringe from being injected along with prefilled pharmaceutical liquid because the injection liquid gets flowed into a person's bloodstream by a pushing force of a rubber plunger of a syringe which is in close contact with the inner wall of the syringe.

In producing glass injection syringes, minute broken glass particles are generated during a process of cutting off glass tubes at appropriate lengths by using a flame and also a finishing process of forming a crown. The glass particles produced and then scattered around the inner wall of a syringe and finally become stuck to the inner wall of a syringe during a subsequent heat treatment. The above syringes, upon completion of production, are placed to go through with a series of rinsing steps to wash off all the other remaining impurities as well as glass particles adhered to the inner wall of a syringe by utilizing methods such as an ultrasound rinse, an unsaturated ammonium rinse, a TAO neutralization and a purified water rinse, a diluted HCl rinse, a surfactant rinse; however, said glass particles are most of the time hardly removed.

The conventional methods of rinsing a glass syringe are described hereunder.

1) Spray pressed air into the inner wall of a glass syringe with the air pressure of 6–7 kg/cm$^2$. (Unable to remove glass particles.)
2) Add surfactants into an ultrasound rinsing equipment, rinse the glass syringes for 4 hrs and finally rinse with purified water. (Unable to remove glass particles.)
3) Immerse said glass syringes in 50% acryl #25, a surfactant, for 2 hrs and then rinse them in an automatic washer at water pressure of 6 kg/cm$^2$ and air pressure of 7 kg/cm$^2$. (Unable to remove glass particles.)
4) Sterilize with steam water at high temperature of 121° C. for 45 min and then rinse with water and air under the pressure of 6 kg/cm$^2$ and 7 kg/cm$^2$ respectively. (Unable to remove glass particles.)
5) Immerse said glass syringes in diluted HCl for 2 hrs and rinse. (Unable to remove glass particles.)
6) Reciprocate with a silicon-rubber plunger made properly fit into the inner wall of a glass syringe. (Unable to remove glass particles because the diameter of the inner wall of each syringe is not usually uniformly made throughout the inner channel of the entire cartridge.)
7) Reciprocate with a sponge plunger made properly fit into the inner wall of a glass syringe. (Unable to remove glass particles because the sponge plunger is neither durable nor practical.)
8) Reciprocate with a wool brush. (Can remove large glass particles and other impurities but unable to remove minute glass particles.)
9) Reciprocate with a stainless steel wire brush. (Unable to remove minute glass particles and also produces scratches on the inner wall of a syringe.)

In general, the glass particles are of various sizes ranging from 3–60 $\mu$m or above. Particles with a size smaller than 30–50 $\mu$m are invisible to the naked eyes and thus have to be examined by using an automatic impurity detector. However, the above equipment is designed to detect only moving particles and is not suitable to detect glass particles that are adhered to the inner wall of a syringe. In the above-mentioned prefilled syringes, the glass particles adhered to the inner wall of a syringe and smaller than 40 $\mu$m, which is approximately the same size of the inner diameter of an injection needle, will be immediately delivered into a human body along with a pharmaceutical liquid during an injection and cause a variety of serious side-effects when accumulated in a reticuloendothelial system such as liver, spleen and lungs. Thus it is highly urgent to find out a solution to prevent patients from being kept vulnerable to medical malpractice.

SUMMARY OF THE INVENTION

The present invention relates to a method to remove minute glass particles generated during a process of manufacturing glass injection syringes which are later adhered to the inner wall of said syringes. The glass particles are then very likely to be delivered into a person's bloodstream during an injection along with a given pharmaceutical liquid in that they are too small to be detected by visual inspections and are also not easily removed by normal rinsing procedures. Therefore, the present invention, which enables to completely get rid of all the glass particles remaining in the inner wall of glass injection syringes after production, can provide ways to improve manufacturing process in pharmaceutical industry in terms of both quality and cost by much reducing product loss as well as to enhance public health control.

DETAILED DESCRIPTION OF THE PREFERRED EMBODIMENT

The main object of the present invention is to remove all the glass particles adhered to the inner wall of a prefilled glass injection syringe. In general, minute glass particles adhered to the inner wall of a glass syringe are hardly detectable and are also not easily washed off by regular detergents. In the present invention, however, the above glass particles are completely removed by using either a brush-type or a stone-type remover which are designed to rotate up and down inside a glass cartridge operated by a motor.

The overall scheme of the present invention is delineated in more detail hereunder.

Figure 1:
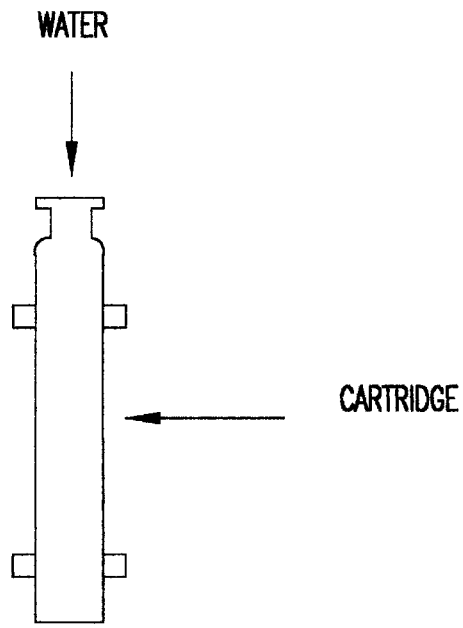
FIG. 1 shows a schematic diagram of a brush-type glass particle remover designed in the present invention.
Figure 1:
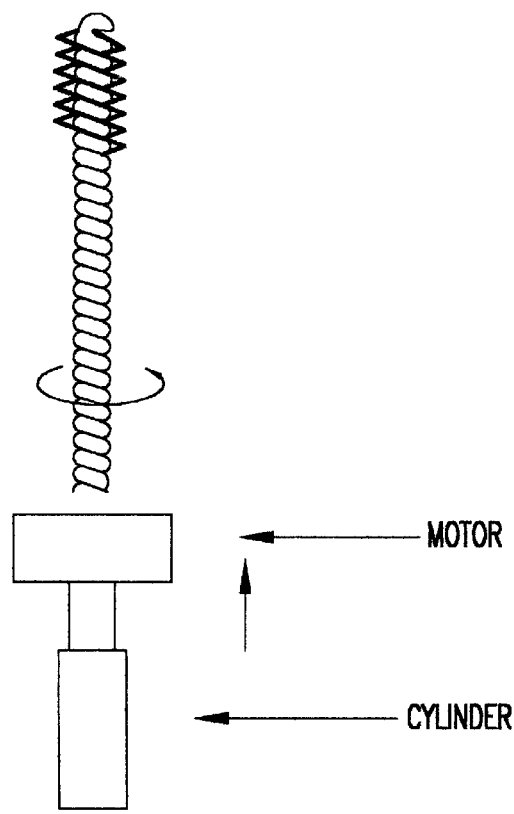
Figure 2:
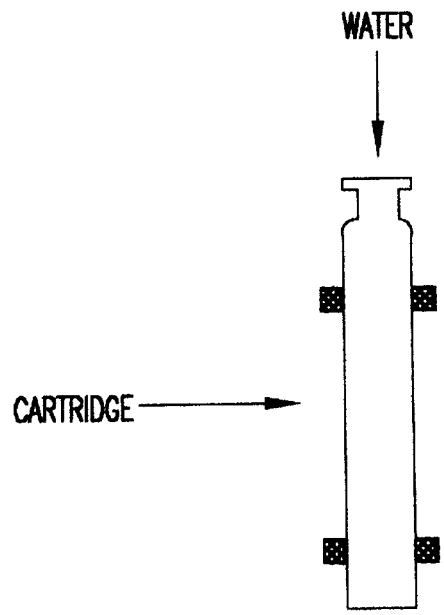
FIG. 2 shows a schematic diagram of a stone-type glass particle remover designed in the present invention.
Figure 2:
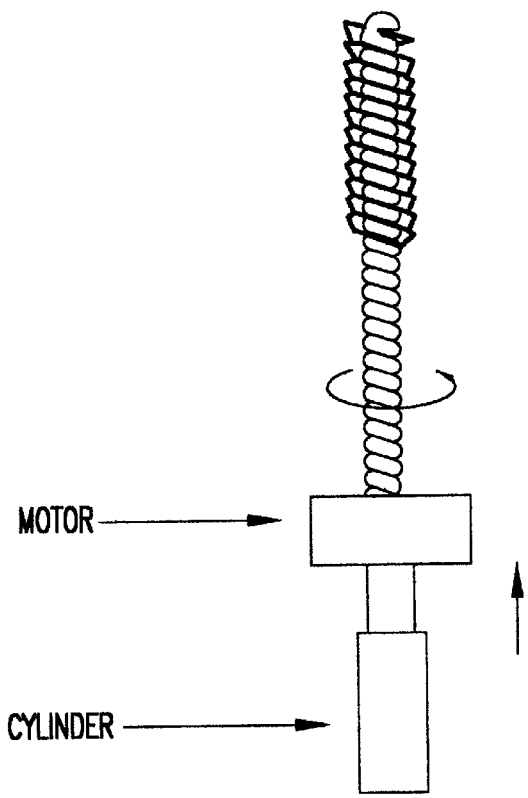

In the present invention, glass particles, still remaining in the inner wall of an injection syringe after production, can be removed by a helical brush-type remover with a proper length and a diameter which is made of polyhexamethylene dodecanediamine, a nylon 6,12. FIG. 1 shows a helical brush-type remover which is inserted into a glass cartridge of an injection syringe and rubbed against the inner wall of said glass cartridge by rotating up and down by a motor while during which purified water is being sprayed into the inner wall of the injection syringe. Another method to remove glass particles displayed in the present invention is to insert a helical stone-type remover with a proper length and a diameter, as illustrated in FIG. 2. The helical stone-type remover is made of aluminum oxide and titanium oxide and is flexibly supported by many internally located stone balls. The helical stone-type remover is inserted into a glass cartridge of an injection syringe and rubbed against the inner wall of said glass cartridge by rotating up and down by a motor while during which purified water is being sprayed into the inner space. Here, the stone balls should be molded to a plastic pin with a proper elasticity so that the entire pin containing stone balls can be elastically bent to some extent when inserted into a glass cartridge.

The methods of producing and rinsing glass cartridges used for injection syringes are as follows.

1) Preliminary glass cartridges are produced and cut off at appropriate lengths by using a flame and the inside of each glass cartridge gets cleaned by passing pressed air through the internal space of each glass cartridge.
2) Rinse said glass cartridges with clean water or steam, dry and pack.
3) Process said glass cartridges further to form both a crown and a flange by using a flame.
4) Rinse off said glass particles produced and adhered to the inner wall of glass tubes in the above step with clean water a few times, rewash with ammonium fluoride and finally rinse with purified water a few times.
5) Dry the above glass cartridges at 60° C. or above and pack. (The glass cartridges obtained in this step still contain glass particles smaller than 30 µm in size which are adhered to the inter wall of said cartridges.)
6) Insert either a brush-type remover or a stone-type remover into a glass cartridge and rinse off any impurities including small glass particles by rotating the remover up and down through the inner cartridge at the speed of 5–10 rpm while spraying purified water into the inner wall of a glass cartridge. (The remover can be also manually operated but it is more preferred to use a water-proof motor to improve the workability as well as the rinse effect. Here, one end of the glass particle remover should be clamped to the shaft of the water-proof motor.)
7) Rinse the above glass cartridges further with purified water, pressed air, distilled water and pressed air in this order.

The resulting glass cartridges passed through the removal steps of the present invention described above become free of glass particles adhered to the inner wall of glass cartridges and the inner walls of glass cartridges are also well prevented from scratches. The above methods to remove glass particles can be applied during the process of producing preliminary glass tubes produced prior to forming glass cartridges for injection syringes as well as during the process of manufacturing glass cartridges themselves, and by performing double rinse in two different manufacturing steps glass particles can be completely removed.

The results of rinses according to the methods of the present invention are shown below in Table 1.

TABLE 1

| | Number of Glass Cartridges Examined | Glass Cartridges With Glass Particles | Glass Cartridges without Glass Particles | Methods of Examination |
| --- | --- | --- | --- | --- |
| Before Rinse | 1,000 | 280 | 720 | Visual Inspection |
| After Rinse | 1,000 | 0 | 1,000 | Visual Inspection |

*Rinse condition (1) pressure of purified water: 5–5.5 kg/cm$^2$
(2) temperature of purified water: 65–70° C.
(3) air pressure: 5 kg/cm$^2$
(4) number of glass cartridges rinsed: 100–120/min The conventional glass injection syringes which have been used in hospitals have the drawback that there are impurities of small glass particles still remaining adhered to the inner wall of a glass syringe after production and later being delivered into a person's bloodstream during an injection along with a given pharmaceutical liquid pushed by a rubber plunger of a syringe which is in very close contact with the inner wall of the syringe. This has been raising a critical issue in a medical field since said glass particles, when accumulated in a reticuloendothelial system such as liver, spleen and lungs, can lead to develop a variety of serious side-effects such as clogging of blood capillaries. Therefore, the methods to completely remove said glass particles using either a brush-type or a stone-type remover as disclosed in the present invention can provide ways to innovate manufacturing process in pharmaceutical industry in terms of both quality and cost by much reducing product loss as well as to enhance public health control.

What is claimed is:

1. A method of removing glass particles remaining on an inner wall of a glass cartridge of an injection syringe after production of said glass cartridge, said method comprising the steps of:

a) providing a helical brush remover which is made polyhexamethylene dodecanediamide;
   b) inserting said helical brush remover into an inner wall of said glass cartridge of said injection syringe;
   c) rubbing said helical brush remover against said inner wall of said glass cartridge by rotating said helical brush remover up and down said inner wall of said glass cartridge, wherein said rubbing step removes glass particles remaining on said inner wall of said glass cartridge of said injection syringe; and
   d) rinsing said inner wall of said glass cartridge by spraying purified water onto said inner wall of said glass cartridge during said rubbing step.

2. A method of removing glass particles remaining on an inner wall of a glass cartridge of an injection syringe after production of said glass cartridge, said method comprising the steps of:

a) providing a helical stone remover which is made of aluminum oxide and titanium oxide;
b) inserting said helical stone remover into an inner wall of said glass cartridge of said injection syringe;
c) rubbing said helical stone remover against said inner wall of said glass cartridge by rotating said helical stone remover up and down said inner wall of said glass cartridge, wherein said rubbing step removes glass particles remaining on said inner wall of said glass cartridge of said injection syringe; and
d) rinsing said inner wall of said glass cartridge by spraying purified water onto said inner wall of said glass cartridge during said rubbing step.

\* \* \* \* \*